United States Patent [19]

Holtkamp

[11] Plant 4,500

[45] Feb. 5, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "OPTIMARA", Isselburg, Fed. Rep. of Germany

[21] Appl. No.: 966,225

[22] Filed: Dec. 4, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African violet known by the cultivar name Iowa and particularly characterized by the combined features of single, violet-shaped flowers having an intensive blue-violet color; strong and upright flower stems rising from the center of the plant so as to carry the bouquet centrally and well above the foliage; and by its vigorous growth and compact habit.

1 Drawing Figure

The present invention comprises a new and distinct cultivar of African violet plant, botanically known as *Saintpaulia ionantha,* and hereinafter referred to by the cultivar name Iowa. The new cultivar, identified during the breeding and selection process by the designations b. 242/3 and 15/78, is a product of a planned breeding program. Iowa is characterized principally by its regular violet shaped, non-dropping flowers, the flowers are carried on strong and straight stems out of the center of the plant. The leaves are dark green with reddish underside, and the flower color is an intensive blue-violet color. These traits in combination were not present in previously available commercial cultivars.

The new cultivar was originated from a cross made in a controlled breeding program in Isselburg, Rhineland, Germany. The female, or seed parent is known by the designation Zsu/Bie/vio, and is not patented. The male, or pollen parent was XVX 249, also unpatented.

The new cultivar Iowa was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Iowa, which in combination distinguish this African violet as a new and distinct cultivar:

(1) Single, violet-shaped flowers.

(2) Intensive blue-violet color.

(3) Very strong and upright flower stems.

(4) 7–9 flower stems out of the center of the plant whereby the bouquet is elevated centrally well above the foliage.

(5) Compact growth habit.

The accompanying photographic drawing shows a typical specimen plant of the new cultivar. The colors appearing in the photograph are as true as possible with color illustrations of this type.

In the following description, color references are made to the Royal Horticultural Society (R.H.S.) color chart, except where general color terms of ordinary significance are obvious.

Botanical classification: *Saintpaulia ionantha,* Ramat. cv Iowa

Parentage:

*Male parent.*—XVX 249.

*Female parent.*—Zsu/Bie/vio.

Propagation: The new cultivar holds its distinguishing characteristics through successive propagations by leaf cuttings and by division of shoots.

Plant: From 8 cm. to 10 cm. tall when grown in pots, and approximately 25 cm. in diameter when fully grown.

*Leaves.*—General form: oblong to round. Diameter: 50–60 mm. Texture: slightly soft, hairy. Veins: well pronounced; reddish in color. Color (upperside): 147A. Color (underside): 186A. Petiole: red-brown.

Flower:

*Buds.*—6–7 mm., round shape.

*Sepals.*—Five, spear shape. Color: 187A. Calyx: with receptacle and seed vessel joined. Aspect: funnel-shaped. Peduncle: strong, straight 20–25 mm.

Individual flowers:

*Size.*—35–37 mm. in total diameter.

*Color.*—Upperside: 89A. Underside: 89 C–D.

*Borne.*—Up to 6 flowers per stem.

*Shape.*—Five petals, two small and three large.

*Corolla.*—*The two small petals are* 19 mm. long and 16 mm. wide; the three large petals are 16 mm. long and 12 mm. wide.

*Arrangement.*—The flowers are carried on strong and upright stems, with six or more flowers being carried on each stem.

*Flowering time.*—First flowers appear 7–8 weeks after potting; in 9–10 weeks plant is in full bloom.

Reproductive organs:

*Stamens.*—Two in number.

*Anthers.*—Four anthers, color 7B.

*Arrangement.*—The stamens are underneath the seed vessel and are joined to the receptacle by two short stems.

*Filaments.*—3–5 mm. long.

*Styles.*—Red-violet in color.

*Pollen color.*—7-C.

Roots: Root system well developed, white if young and active, turning brownish as plant matures.

Disease resistance: No problem noticed to date.

General observations: Iowa is a very vigorous growing variety with compact habit. The flowers are on strong upright stems extending from the center of the plant, and the flowers are very intensive blue-violet in color. The position of the bouquet in a raised central portion above the foliage presents a distinct appearance.

I claim:

1. A new and distinct cultivar of African violet known by the cultivar name Iowa and particularly characterized by the combined features of single, violet-shaped flowers having an intensive blue-violet color; strong and upright flower stems rising from the center of the plant so as to carry the bouquet centrally and well above the foliage; and by its vigorous growth and compact habit.

* * * * *

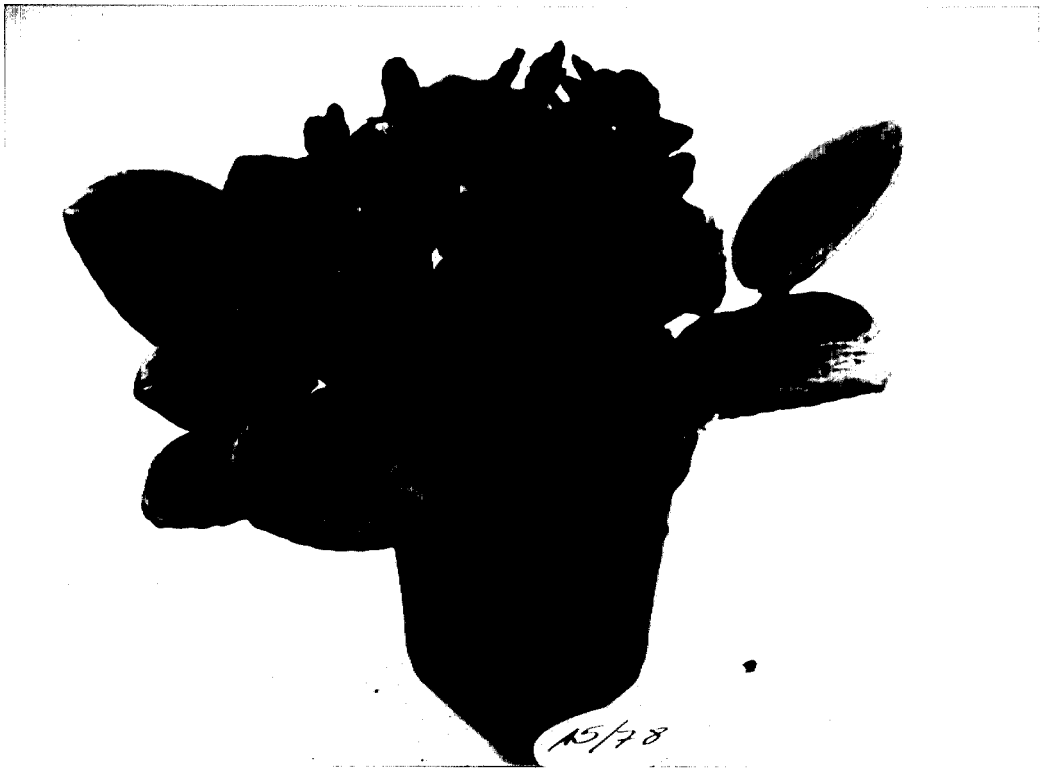
15/78